US006966922B2

(12) United States Patent
Grahn et al.

(10) Patent No.: US 6,966,922 B2
(45) Date of Patent: *Nov. 22, 2005

(54) METHODS AND DEVICES FOR PREVENTION OF HYPOTHERMIA IN A MAMMAL DURING PROLONGED EXPOSURE TO EXTREME COLD

(75) Inventors: Dennis A. Grahn, Palo Alto, CA (US); H. Craig Heller, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 23 days.

This patent is subject to a terminal disclaimer.

(21) Appl. No.: 10/655,557

(22) Filed: Sep. 3, 2003

(65) Prior Publication Data

US 2004/0133253 A1      Jul. 8, 2004

Related U.S. Application Data

(63) Continuation of application No. 09/877,407, filed on Jun. 7, 2001, now Pat. No. 6,673,099.

(60) Provisional application No. 60/210,664, filed on Jun. 9, 2000.

(51) Int. Cl.[7] .............................................. A61F 7/00
(52) U.S. Cl. ...................................... 607/104; 607/114
(58) Field of Search ............................... 607/104, 108, 607/109, 114, 96; 601/6, 11, 16

(56) References Cited

U.S. PATENT DOCUMENTS

| 4,149,529 | A | | 4/1979 | Copeland et al. |
| 5,074,285 | A | | 12/1991 | Wright |
| 5,358,467 | A | | 10/1994 | Milstein et al. |
| 5,683,438 | A | * | 11/1997 | Grahn ......................... 126/204 |
| 5,688,225 | A | | 11/1997 | Walker |
| 6,149,674 | A | * | 11/2000 | Borders ....................... 601/148 |

FOREIGN PATENT DOCUMENTS

| WO | WO 98 40039 | 9/1998 |
| WO | WO 98/40039 | 9/1998 |
| WO | WO 99/23980 | 5/1999 |

OTHER PUBLICATIONS

Bergersen et al., "Perfusion of the human finger during cold-induced vasodilation" *American Physiological Society* R731-R737 (1999).

Bergersen et al., "Local constriction of arteriovenous anastomosis in the cooled finger" *American Physiological Society* R880—R886 (1997).

(Continued)

*Primary Examiner*—Roy D. Gibson
(74) *Attorney, Agent, or Firm*—Bret E. Field; Bozicevic, Field & Francis LLP

(57) ABSTRACT

Methods and devices for preventing a change in the core body temperature of a mammal under cold conditions are provided. In the subject methods, a requirement for thermal energy input in said mammal is first detected. In response to the detection of this requirement for thermal energy input, a surface of a portion of the mammal is contacted with a warm temperature medium under negative pressure conditions for a period of time sufficient to introduce thermal energy into the core body of the mammal. The subject devices include at least a means for detecting a requirement for thermal energy input and a means for contacting a surface of the mammal with a warm temperature medium under negative pressure conditions. The subject methods and devices find use in a variety of applications, and are particularly suited for use in maintaining the core body temperature of a mammal substantially constant under cold conditions for an extended period of time.

27 Claims, 4 Drawing Sheets

OTHER PUBLICATIONS

Bergersen et al., "Effect of local warming on hand and finger artery blood velocities" *American Physiological Society* R325-R330 (1995).

Dennis Grahn et al. "Recovery from mild hypothermia can be accelerated by mechanically distending blood vessels in the hand" (1998) *The American Physiological Society*, pp 1643-1648.

Eldar Soreide et al. "A Non-invasive means to effectively restore normothermia in cold stressed individuals: A Preliminary Report" *The Jouranl of Emergency Medicine*, vol. 17 No. 4, pp. 725-730 (1999).

Wachter, "New Device Could Reduce Rewarming Time from Anethesia Hypothermia," Anesthesiology News (1997), p. 1.

"Hypothermia Rewarmer Launched in Postoperative Market (Dec. 4, 1998)," MDI Business Advisor (1998).

Thermo-STAT Operations Manual, Aquarius Medical Corporation, (1998).

* cited by examiner (SECTION A-A)

(SECTION B-B)

METHODS AND DEVICES FOR PREVENTION OF HYPOTHERMIA IN A MAMMAL DURING PROLONGED EXPOSURE TO EXTREME COLD

CROSS-REFERENCE TO RELATED APPLICATIONS

This application is a continuation of U.S. patent application Ser. No. 09/877,407 filed 07 Jun. 2001, now U.S. Pat. No. 6,673,099, which claims the benefit of the filing date of the U.S. Provisional Patent Application Ser. No. 60/210,664 filed Jun. 9, 2000; the disclosures of which are herein incorporated by reference.

1. Field of the Invention

The field of this invention is core body energy regulation.

2. Background of the Invention

Prolonged exposure to cold environmental conditions for extended periods of time can result in a condition known as hypothermia which can manifest itself in a variety of symptoms. The onset of symptoms is usually slow; there is likely to be a gradual loss of mental acuity and physical ability. The person experiencing hypothermia, in fact, may be unaware that he or she is in a state that requires emergency medical treatment. Symptoms include: apathy or lethargy, confusion, drowsiness, loss of coordination, pale and cold skin, shock, slowing of breathing, slurred speech, uncontrollable shivering, and weakness. As such, prolonged exposure to cold environmental conditions can result in significant adverse physical and mental effects.

There are a number of situations where it is desirable for a person to be exposed to cold environmental conditions for extended periods of time. For example, there are professions which require individuals to work under cold conditions, where such professions include, but are not limited to: professions that require prolonged time spent underwater, professions that require prolonged time spent outdoors in cold climates, and the like.

As such, there is great interest in the development of a technology that can maintain the core body temperature of a mammal at a substantially constant value for prolonged periods of time under cold conditions. Of particular interest would be the development of such a technology that accomplished the above results in a manner that was well-tolerated by the host, e.g., in a non-invasive manner that did not substantially impair the ability of the host to perform various tasks, e.g., work related tasks.

RELEVANT LITERATURE

U.S. Pat. No. 5,683,438. See also WO 98/40039. Also of interest are: Soreide et al., "A non-invasive means to effectively restore normothermia in cold stressed individuals: a preliminary report," J Emerg. Med. (1999 July–August)17 (4):725–30 and Grahn et al., "Recovery from mild hypothermia can be accelerated by mechanically distending blood vessels in the hand," J. Appl Physiol. (1998) 85(5):1643–8.

SUMMARY OF THE INVENTION

Methods and devices for preventing a change in the core body temperature of a mammal under cold conditions are provided. In the subject methods, a requirement for thermal energy input in said mammal is first detected. In response to the detection of this requirement for thermal energy input, a surface of a portion of the mammal is contacted with a warm temperature medium under negative pressure conditions for a period of time sufficient to introduce thermal energy into the core body of the mammal. The subject devices include at least a means for detecting a requirement for thermal energy input and a means for contacting a surface of the mammal with a warm temperature medium under negative pressure conditions. The subject methods and devices find use in a variety of applications, and are particularly suited for use in maintaining the core body temperature of a mammal substantially constant under cold conditions for an extended period of time.

DESCRIPTION OF THE SPECIFIC EMBODIMENTS

Figure 1:
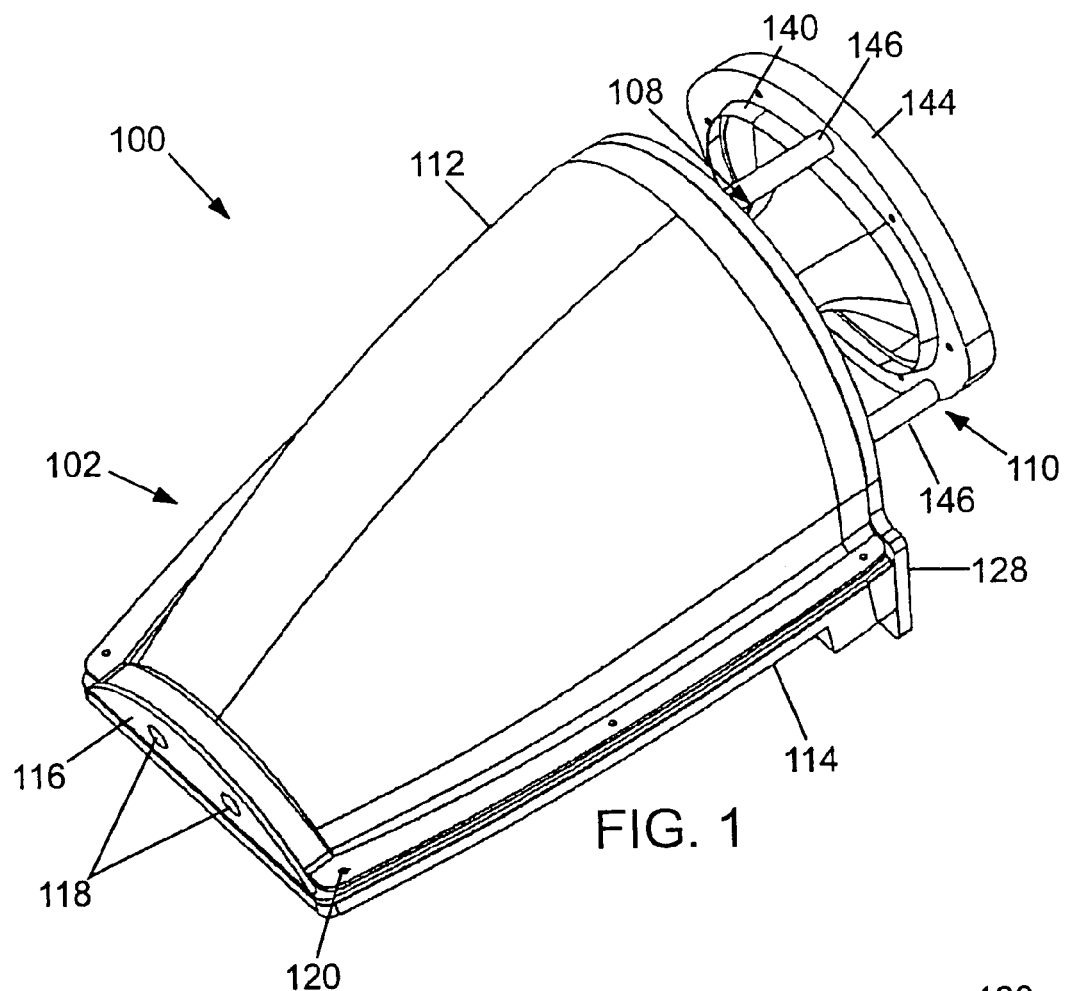
FIGS. 1 to 6 provide various views of a device that can be employed to practice to the subject methods.

Methods and devices for preventing a change in the core body temperature of a mammal under cold conditions are provided. In the subject methods, a requirement for thermal energy input in said mammal is first detected. In response to the detection of this requirement for thermal energy input, a surface of a portion of the mammal is contacted with a warm temperature medium under negative pressure conditions for a period of time sufficient to introduce thermal energy into the core body of the mammal. The subject devices include at least a means for detecting a requirement for thermal energy input and a means for contacting a surface of the mammal with a warm temperature medium under negative pressure conditions. The subject methods and devices find use in a variety of applications, and are particularly suited for use in maintaining the core body temperature of a mammal substantially constant under chronic exposure to cold conditions for an extended period of time. In further describing the subject invention, the subject methods and devices will be discussed in greater detail, followed by a review of representative applications in which the subject methods and devices find use.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

METHODS

As summarized above, the subject invention provides methods for preventing a change in the core body temperature of a mammal under cold conditions. More specifically, the subject methods prevent a significant decrease in the core body temperature of a mammal from occurring under cold conditions. By "significant decrease" is meant a decrease in brain temperature of a magnitude of at least about 1, usually at least about 1.5 and more usually at least about 2° C. In many embodiments, as described in more detail below, the subject methods are methods of maintaining the core body temperature of a mammal at a substantially constant value under cold conditions for an extended period of time. By "maintaining at a substantially constant value" is meant that the core body temperature of the mammal does not vary during the extended period of time by more than an insubstantial amount, where by "insubstantial amount" is meant an amount ranging from about 0.2 to 5.0, usually from about 0.5 to 4.0 and more usually from about 1.0 to 2.0° C. The subject methods are meant to be employed under cold environmental conditions. By "cold environmental" is meant conditions that produce hypothermia in a mammal, i.e., hypothermia producing conditions, when a mammal is exposed to the conditions for at least about 5 min, usually at least about 60 min. The temperature of the conditions may vary depending on the nature of the conditions, e.g. in air, underwater, etc., but will generally be less than about 30, usually less than about 25 and more usually less than about 20.

In practicing the subject methods, the first step is to detect a requirement in the mammal for input of thermal energy. More specifically, the first step is to detect a need in the mammal for an input of thermal energy in order to prevent a decrease in the core body temperature of the mammal. This requirement for thermal energy input may be detected using any convenient protocol. One convenient protocol is to detect a thermoregulatory error in the mammal. By thermoregulatory error is meant an error in the thermoregulation of the mammal such that various physiological changes occur in the mammal in response to the error. The thermoregulatory error may be detected by detecting one or more of the physiological changes associated with the error. Physiological changes of interest include: change in temperature, vasoconstriction, change in blood pressure, tremor activity, and the like. Involved in this portion of the claimed methods is a data processing step for processing the thermal energy requirement data and activating the contact with the warm temperature medium in response thereto (as described in greater detail below), e.g., a step of using a computing means that controls the contact of the heat exchange surface with the warm temperature medium.

Following detection of the requirement for thermal energy input, thermal energy is input into the core body of the mammal. By core body is meant the internal body region or portion of the mammal, as opposed to the surface of the mammal. In inputting or introducing thermal energy or heat into the core body of the mammal, a surface of the mammal is contacted with a warm temperature medium under negative pressure conditions for a period of time sufficient to achieve the desired amount of heat introduction. The surface that is contacted with the warm temperature medium is generally a heat exchange surface which acts as a heat exchange means between the core body and the environment of the mammal. Heat exchange surfaces of interest with the subject methods include those found in the various regions of the mammal, e.g., the arms, legs, palms, soles, head, face, ears, and the like.

By negative pressure conditions is meant a pressure lower than ambient pressure under the particular conditions in which the method is performed, e.g., 1 ATM at sea level. The magnitude of the decrease in pressure from the ambient pressure under the negative pressure conditions is generally at least about 10 mmHg, usually at least about 20 mmHg and more usually at least about 35 mmHg, where the magnitude of the decrease may be as great as 85 mmHg or greater, but typically does not exceed about 60 mmHg and usually does not exceed about 50 mmHg. When the method is performed at or about sea level, the pressure under the negative pressure conditions generally ranges from about 740 to 675 mmHg, usually from about 730 to 700 mmHg and more usually from about 725 to 710 mmHg.

As mentioned above, the surface of the mammal is contacted with a warm temperature medium under the negative pressure conditions. By warm temperature medium is meant a medium that has a temperature which is sufficient to provide the requisite or desired core body thermal energy input or introduction. The nature of the medium may vary, the medium being a temperature controlled solid material, e.g., warming blanket; a liquid; or gas; depending on the particular device employed to practice the subject methods. The temperature of the warm temperature medium may vary. The warm temperature medium generally has a temperature ranging from about 40 to 52, usually from about 42 to 50 and more usually from about 44 to 48° C.

Contact is maintained for a period of time sufficient for the desired amount of core body thermal energy input or introduction to occur. As such, contact is generally maintained for at least about 1 min, usually at least about 2 min and more usually at least about 3 min, where contact may be maintained for up to 10 hrs or longer, but is generally not maintained for longer than 1 day and usually is not maintained for longer than 1 hr.

In practicing the subject methods, the negative pressure conditions during contact may be static/constant or variable. Thus, in certain embodiments, the negative pressure is maintained at a constant value during contact of the surface with the low temperature medium. In yet other embodiments, the negative pressure value is varied during contact, e.g., oscillated. Where the negative pressure is varied or oscillated, the magnitude of the pressure change during a given period may be varied may range from about −85 to 40 mmHg, usually from about −40 to 0 mmHg, with the periodicity of the oscillation ranging from about 0.25 sec to 10 min, usually from about 1 sec to 10 sec.

In practicing the subject methods, the negative pressure conditions may be provided using any convenient protocol. In many embodiments, the negative pressure conditions are provided by enclosing a portion of the mammal that includes the target surface that is to be contacted with the low temperature medium in a sealed enclosure, where the pressure is then reduced in the sealed enclosure thereby providing the requisite negative pressure conditions. The portion that is enclosed in the sealed enclosure is a portion of the mammal that includes the target heat exchange surface, and therefore is an appendage in many embodiments of the subject invention. As such, the portion that is sealed is an arm or leg, or at least a portion thereof, e.g., hand or foot, in many embodiments of the subject invention. The nature of the enclosure will vary depending on the nature of the appendage to be enclosed, where representative enclosures include gloves, shoes/boots, or sleeves, where the latter is described in greater detail supra in connection with the description of the representative devices that can be used to practice the subject invention.

The magnitude of core body thermal energy introduction accomplished during practice of the methods may vary, and is sufficient to maintain the core body temperature of the mammal at a substantially constant value. In many embodiments, the magnitude of heat introduction is generally at least about 0.5 Kcal/min, usually at least about 1 Kcal/min and more usually at least about 1.5 Kcal, where the magnitude may be as great as 50 Kcal/min or greater, but generally does not exceed about 30 Kcal/min and usually does not exceed about 15 Kcal/min. The period of time that the heat is introduced into the core body may vary, but typically ranges from about 1 min to 24 hrs, usually from about 2 min to 10 hrs and more usually from about 2 min to 5 hrs.

In the subject methods, the above described steps may be performed a single time or a plurality of times over any given time period, i.e., they may be performed once during a given time period or iterated 2 or more times during a given time period. Where the above steps are performed two or more times during a given time period or temporal duration, the multiple detecting steps may take the form of monitoring the user during the time period in a substantially continuous manner, such that the requirement for thermal energy input is detected as a function of time in a substantially continuous manner.

The subject methods are suitable for use with a variety of mammals. Mammals of interest include, but are not limited to: race animals, e.g., horses, dogs, etc., work animals, e.g., horses, oxen etc., and humans. In most embodiments, the mammals on which the subject methods are practiced are humans.

DEVICES

The above described methods may be practiced using any convenient device. In general, any device that is capable of: detecting a need for thermal energy input, achieving negative pressure and achieving warm temperature medium contact with the target heat exchange surface for the requisite period of time may be employed. The devices employed in the subject methods include a sensing element for detecting a requirement for thermal energy input. This particular sensing element may vary depending on the how the requirement is detected. For example, where the requirement is detected by detecting a thermoregulatory error as manifested by the appearance of vasoconstriction, a thermosensor finds use. Other detection devices of interest include, but are not limited to: pressure sensor, EMG, thermometer, and the like. The devices also generally include a detection element for detecting when thermal energy input is no longer required to maintain the core body temperature of the mammal, where this detection element is often the same as the element for detecting the requirement for thermal energy input.

The subject devices also include a negative pressure element for providing the negative pressure environment at the target heat exchange surface. In many embodiments, this means for providing a negative pressure environment includes a sealing element for sealing an appendage of the mammal in an enclosed environment in which negative pressure conditions can be produced. Representative enclosing means or sealing elements include sleeves, boots/shoes, gloves, etc. which are in operational relationship with a negative pressure inducing means, e.g., a vacuum, that is capable of producing a negative pressure environment, as described above, in the sealed enclosure. The negative pressure inducing element may be actuated in a number of different ways, including through motor driven aspiration, through a system of valves and pumps which are moved through movement of the mammal in a manner sufficient to create negative pressure in the sealed environment, etc.

As mentioned above, the subject devices also include an element for contacting the heat exchange surface with the warm temperature medium. Representative means for contacting the surface with a warming medium include: warming blankets, warm water immersion means, warming gas means, etc. In many embodiments, the device further includes a means for producing the warm temperature medium, where this means may vary depending on the nature of the warm temperature medium. For example, where the warm temperature medium is a warming blanket whose temperature is modulated by actuation of resistance heating elements in the blanket, this means for producing a warm temperature medium is a means for providing electrical current to the warming blanket. Alternatively, where the warm temperature medium is a warm gas, e.g., air, the means for producing the warm medium is a means for warming or heating the gas, e.g. a microfurnace, and the like.

A representative device that can be readily adapted for use in the subject methods is that described in U.S. Pat. No. 5,683,438, the disclosure of which is herein incorporated by reference. In certain embodiments, the devices are adaptations of those devices described in U.S. patent application Ser. No. 09/839,590; the disclosure of which are herein incorporated by reference.

FIGS. 1 to 6 provide various views of another embodiment of a device that can be employed to practice the subject invention. The features of the system depicted in FIGS. 1 to 6, belonging to AVACore Technologies, Inc. (Palo Alto, Calif.), are preferred for carrying out the methodologies described herein. The system described includes a negative pressure chamber in which to apply or remove thermal energy from a human subject. An improved interface between the chamber and its external environment is provided.

Aquarius, Inc. (Scottsdale, Ariz.) produces a system that may be used or variously modified for use in the stated method(s). However, that system utilizes a "hard" seal interface with a user. The system described herein may utilize a "soft" seal. A "hard" seal is characterized as one designed to altogether avoid air leakage past the boundary it provides. In theory, a "hard" seal will allow a single evacuation of the negative pressure chamber for use in the methods. In practice, however, a "hard" seal can produce a tourniquet effect. Also, any inability to maintain a complete seal will be problematic in a system requiring as much.

A "soft" seal as described herein is characterized as providing an approximate or imperfect seal at a user/seal interface. Such a seal may be more compliant in its interface with a user. Indeed, in response to user movement, such a seal may leak or pass some air at the user/seal interface. In a negative-pressure system designed for use with a soft seal, a regulator or another feedback mechanism/routine will cause a vacuum pump, generator, fan or any such other mechanism capable of drawing a vacuum to respond and evacuate such air as necessary to stabilize the pressure within the chamber, returning it to the desired level. Active control of vacuum pressure in real-time or at predetermined intervals in conjunction with a "soft" seal provided significant advantage over a "hard" seal system that relies on simply pulling a vacuum with the hopes of maintaining the same.

A further disadvantage over the Aquarius system has more to do with seal configuration than its barrier function. Entry and exit from the Aquarius seal is difficult. Whether "hard" or "soft" in function, the present system provides a two-sided seal configuration. The meaning of this will be more apparent in view of the following figures and descriptive text.

Figure 2:
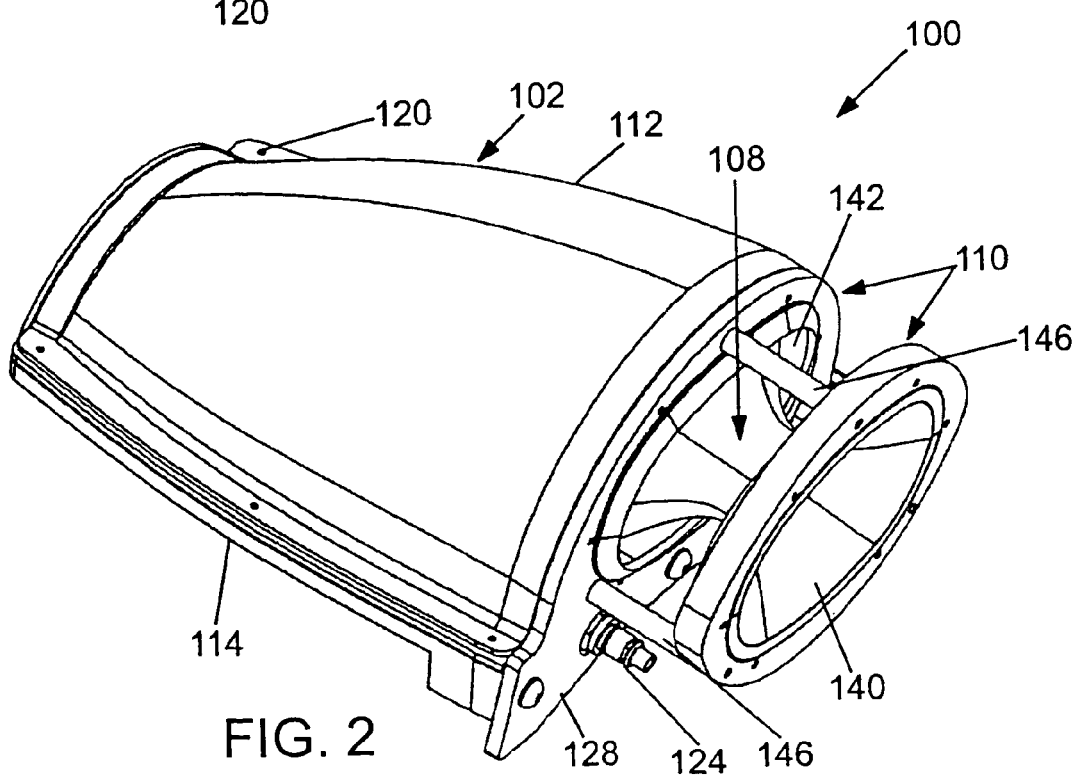
Figure 3:
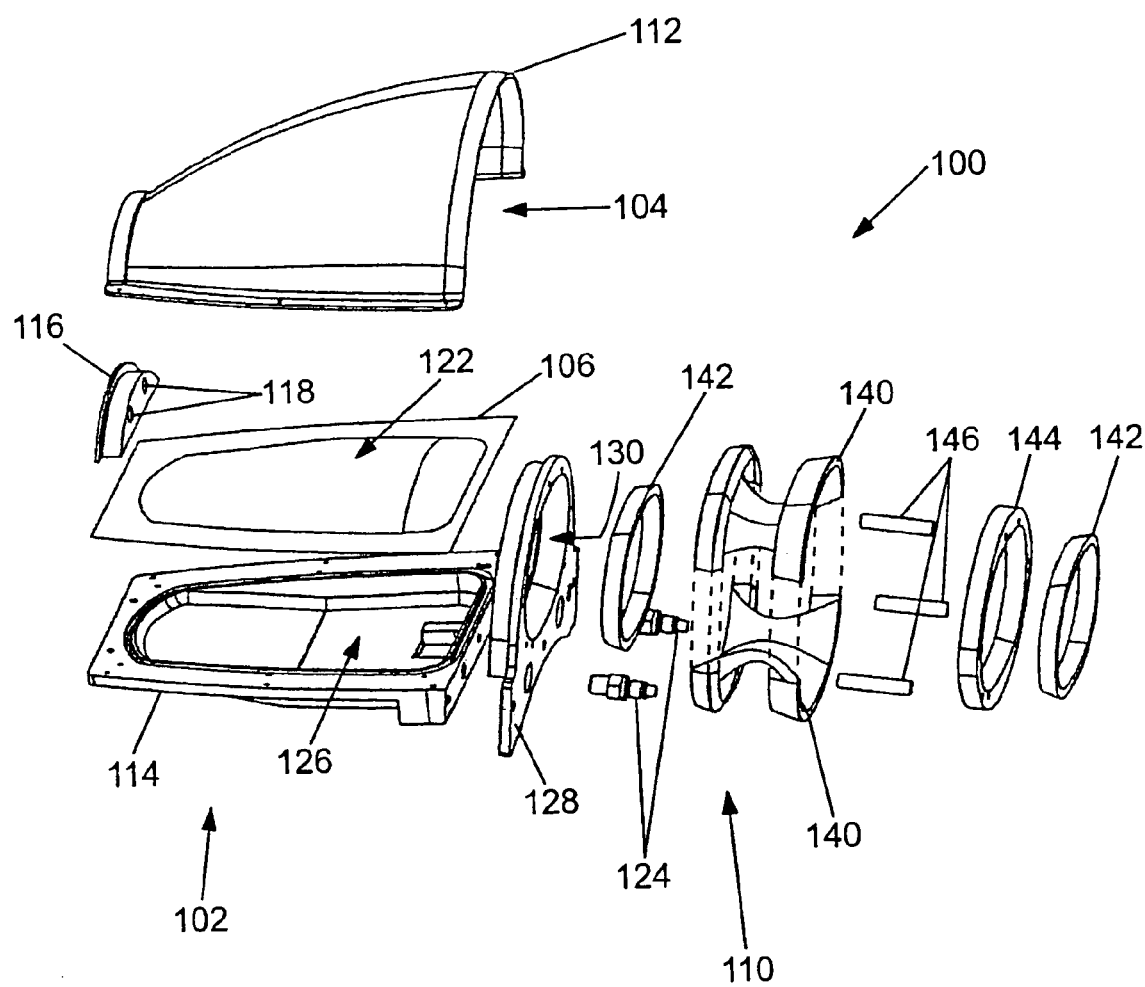

FIGS. 1 and 2 provide fore and aft perspective views of a negative pressure thermal exchange module (100). FIG. 3 provides an exploded view of the same. The system components not shown in the figures include a thermal control or perfusion unit. Such a unit may be adapted to provide a stream of heat exchange media such as water at elevated temperatures, lowered temperatures or both. Further, a vacuum source and regulator optionally used with module (100) are not shown. Any sort of vacuum source or regulator/control mechanism may be used with module (100) as would be apparent to one with skill in the art. Together, these components work to maintain a pressure within module (100) during use between about 20 and 25 inches of $H_2O$ and temperatures for core body cooling between about 19 and 22° C. or temperatures for core body heating between about 40 and 45° C.

As shown, module (100) includes a housing (102) defining a negative pressure chamber (104), a heat-exchange element (106) and a soft, two-sided seal (108) supported by seal frame elements (110).

Housing (102) may be made from a cover (112) and a base (114). Negative pressure chamber (104) is preferably provided between heat exchange element (106) and cover (112). The embodiment shown is adapted to fit the hand of a human user. Chamber (104) is preferably configured to fit a human hand of any size. In order to provide a more space-efficient package, however, it may be more preferably sized to fit 95% of human hand sizes. Alternately, it may be sized for more particularized groups, such as children. It is also contemplated that the housing may be configured to fit a human foot since the under surface of a foot may also be used effectively as a heat exchange surface.

Housing (102) may be constructed from multiple pieces, including an end cap (116) as shown, or it may be provided as a unitary structure. Cap (116) is shown including a ports (118). A first port may be utilized for connection to a vacuum source, while the second may be utilized for a vacuum gauge. Of course, alternate port placement is also possible.

Preferably, housing (102) is made of plastic. Most preferably, the material and design of at least a portion of module (100) are such that housing (102) may be produced by vacuum forming or molding techniques.

Where discrete cover (112) and base (114) portions are used, they may be mechanically secured to one another through bolt holes (120). In such an instance, a gasket or caulking may be employed to seal the periphery of housing (102).

Providing a separable cover (112) and base (114) or heat exchange element (106) provide advantageous access to clean module (100) after use. However, it is contemplated that the top and bottom portions of the module may be fused together, for instance, by ultrasonic welding, chemical bonding or otherwise. Also, as noted above, it is contemplated that housing (102) may be provided in a single piece.

Regardless of the construction, sizing or overall appearance of housing (102), it defines a portion of chamber (104). A heat exchange surface (122) for delivering or accepting a thermal load from a user also defines a portion of chamber (104). A user may directly contact heat exchange surface (122). Alternately, a user may wear a glove or sock or take other prophylactic measures. Heat exchange surface (122) may be provided by a member separate from heat exchange member (106) such as by an intermediate layer of foil, metalized Mylar or another material.

Heat exchange element (106) is preferably made of aluminum or another high thermally-conductive material. It may be in communication with a Peltier device, a desiccant cooling device or an endothermic or exothermic chemical reaction to provide a temperature variance. More preferably, however, heat exchange member (106) is in communication with at an inlet and an outlet (124) to accommodate a flow of perfusion liquid behind heat exchange surface (122). Chilled or heated water may be used to maintain the contact surface of the element at a desired temperature. Optimally, perfusion fluid is run through a series of switchbacks in cavity (126) between element (106) and base (114).

A rear portion of housing (102) and heat exchange member (106) may be provided by plate (128). As depicted, this portion may include provision for inlet and outlet (124) to heat exchange cavity (126) and an opening (130) to chamber (104). A preferred manner of constructing seal (108) is disclosed in connection with plate (128).

Figure 4:
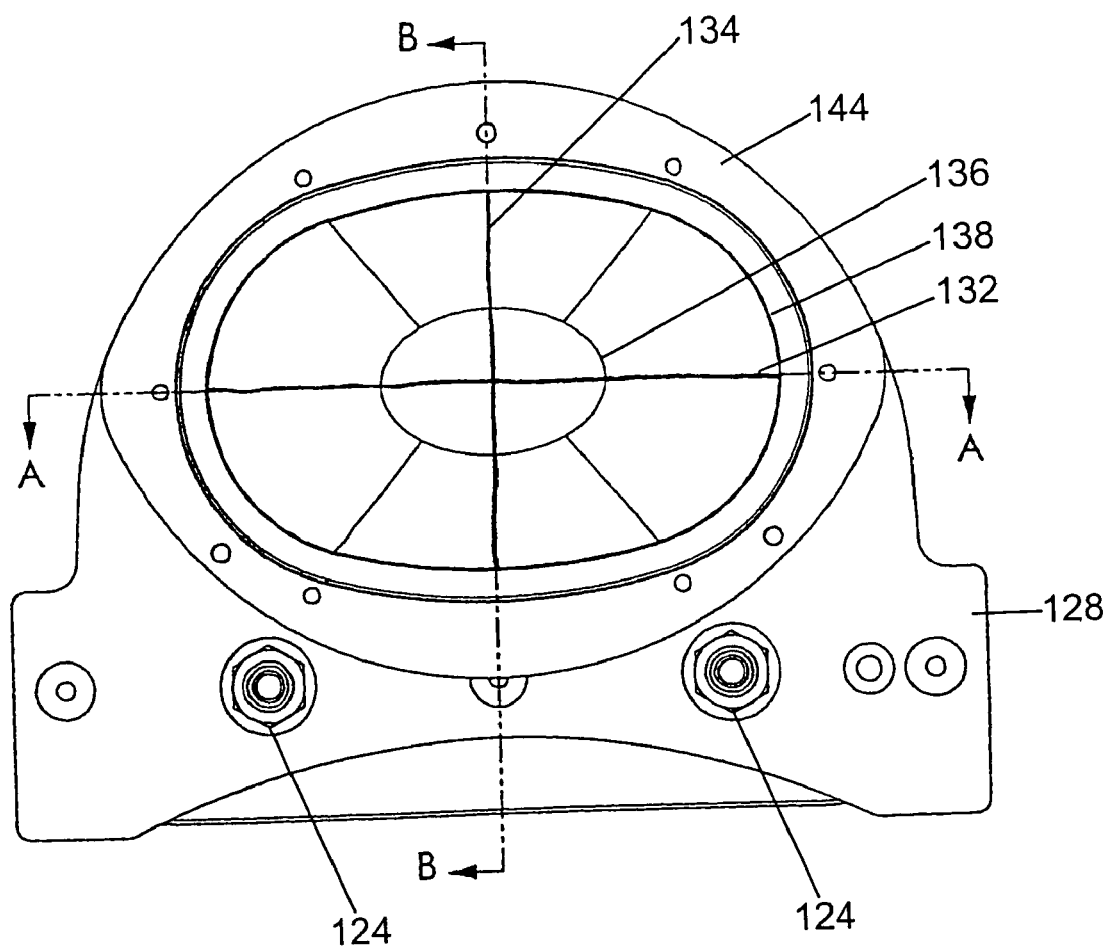
Figure 5:
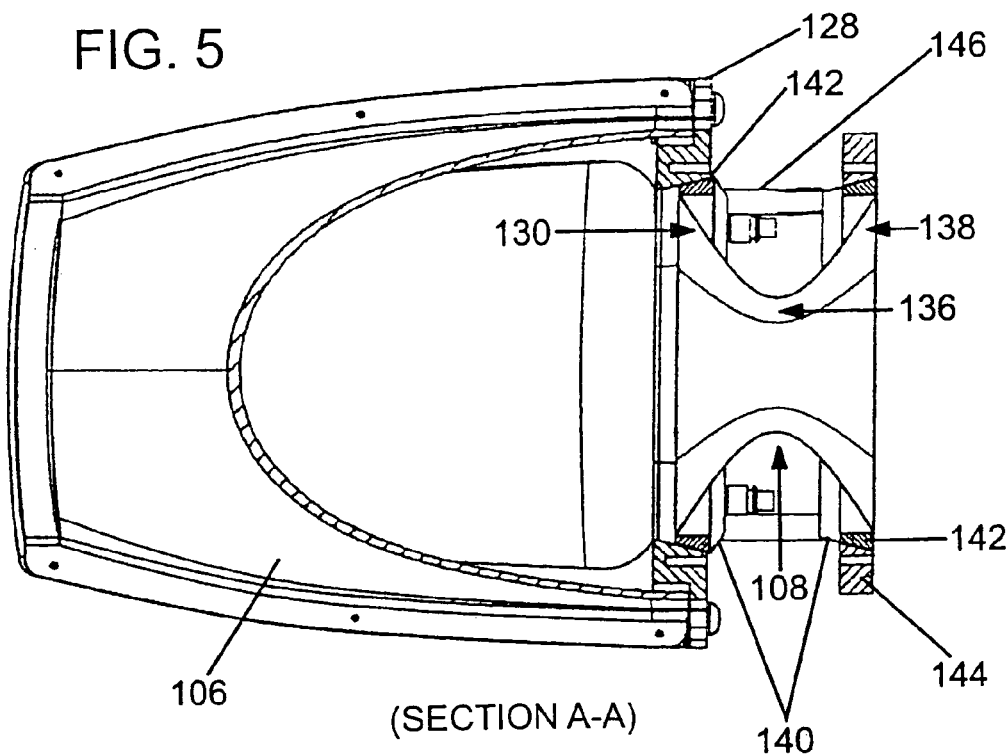
Figure 6:
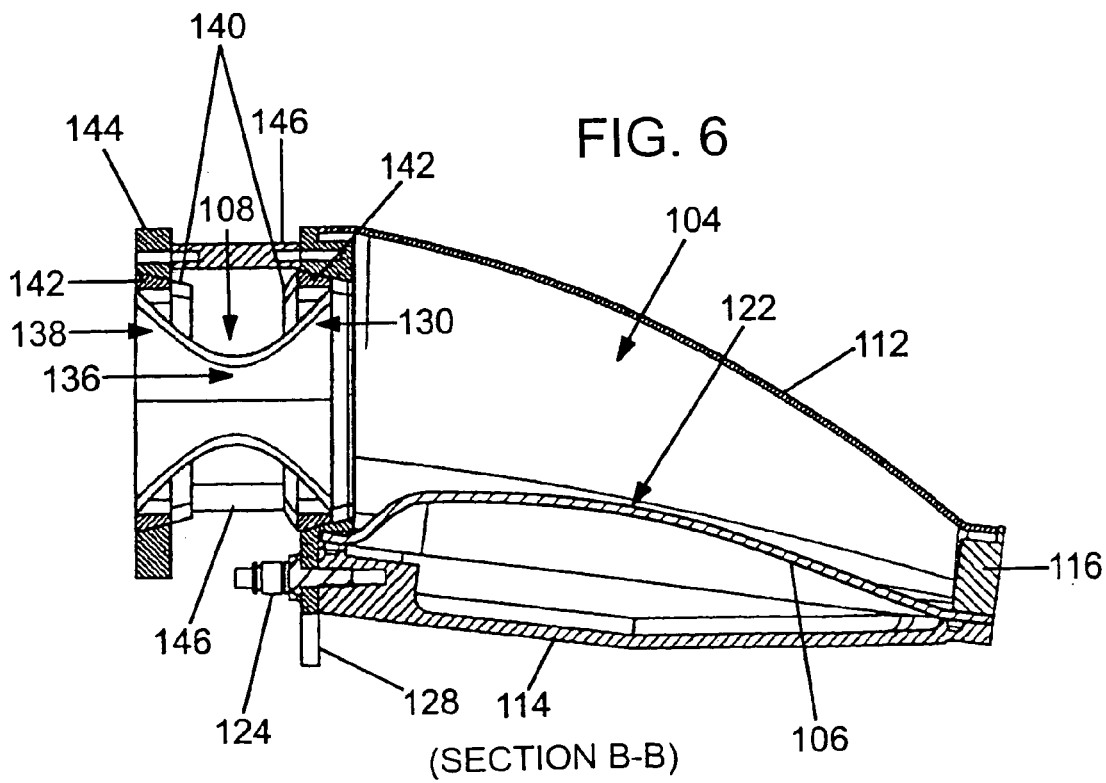

Views detailing preferred geometric aspects of seal (108) are shown in FIGS. 4, 5 and 6. FIG. 4 shows an end-on view of seal (108). Preferably, at least portions of seal (108) are ovalized in form. An elliptical shape may be preferred. A circular shape may also be used. Still, a shape having a major axis (132) and a minor axis (134) will be preferred, at least for the waist opening (136) of seal (108). An ovalized shape approximately corresponds to the shape of the wrist or forearm of a user. A shape having a major axis (132) and a minor axis (134) will also be preferred at chamber opening (130) and seal opening (138). This will assist in providing clearance for hand entry and exit of module (100). It will also simplify the construction of seal webbing (140).

Whether or not ovalized features are utilized for seal (108), it will be shaped roughly like an hourglass. Seal (108) will most closely resemble an hourglass if openings (130), (136) and (138) are circular. When ovalization is applied, different projected views of seal (108)—such as viewed in FIG. 5, for the section taken along line A—A and in FIG. 6 for the section taken along line B—B—display an hourglass shape.

Of course, the shapes depicted may be characterized as other than "hourglass" forms. For instance, profiles of seal (108) may be viewed as hyperbolic or parabolic. Further, simple radiused or semi-circular cross-sections may be utilized in producing seal (108). Further straightened sections may be used, especially, between the openings (130) and (138) and waist (136).

Whatever the case, a two-sided seal with outside openings of a greater size than that of the inside opening is to be used in module (100). This geometry provides for ramps or transition sections for appendage entry and exit. These features assist in stretching the seal interface or waist (136) sufficiently wide to pass a hand or foot both for insertion into and removal from module (100).

Material selection is important in providing such a seal. Clearly, the material must be able to stretch. Further, it should provide a substantial barrier to air flow. To meet each of these criteria, a urethane-backed lycra available from Malden Mills (Malden, Mass.) has proven effective. Still, it is contemplated that other materials may be used. The material (or materials) selected for webbing (140) preferably has a finish that does not grip onto a user so as to complicate entry and exit from module (100). The urethane skin of the referenced material has a satin finish. This decreases friction with the skin and hair of a user.

In addition to providing sufficient stretch, the seal webbing material should also have sufficient strength to avoid being drawn too far into cavity (104) upon the application of vacuum. When in use, the open construction of seal (108) will result in cavity-side webbing material exposed to partial vacuum within chamber (104) to be forced by ambient pressure inward. This self-inflation phenomena observed for the chamber-side of the seal may be of assistance in providing seal patency with a user. However, if too much material bows inward, it will result in an uncomfortable or disconcerting displacement of the user's hand or foot into the device. Accordingly, with proper material choice, the side of seal (108) opposite chamber (104) provides not only a transition section for entry and exit, but also a stabilizing feature for seal position.

Seal (108) is preferably formed by a sleeve made by stitching two pieces of webbing material (140) together where they are shown broken apart in the exploded view of FIG. 3. By constructing the sleeve from two or more pieces, complex shapes can be easily produced. To secure the sleeve webbing (140) in place to form seal (108), it is folded over rings (142) at each end as variously depicted. Then the cavity-side ring and webbing is captured in opening (130) of plate (128). The opposite side of seal webbing (140) is captured between outer ring (142) and retainer member (144). Standoffs (146) or equivalent structure space plate (128) and ring retainer (144) apart to define the overall length of seal (108). Of course, the length of the standoffs or seal may be varied as well as the other parameters of seal (108) that effect fit.

In this respect, it is noted that it may be desirable to provide a longer overall seal in some instances. Increasing overall length provides further design flexibility with seal shape. This may be best taken advantage of by increasing the length of waist (134) to provide greater seal surface contact with a user. This may beneficially reduce any undesirable constricting effects. Furthermore, it is to be appreciated that the nature of the material used for the seal webbing (140) may be advantageously varied. While the noted lycra-based material is isotropic in nature, an anisotropic material or effect may be preferred for the webbing. This is to say that greater radial expansion of the sleeve may be desirable, whereas longitudinal compliance may not be. By reducing compliance along the axis of the sleeve relative to a radial component, it will tend to be drawn into chamber (104) to a lesser degree upon the application of vacuum. For a very high-stretch material, this will allow for smaller seal openings to fit the same population (since they can still stretch webbing (140) radially and have it return sufficiently to form a desired seal), without forfeiting the full set of advantages that the two-sided seal described offers.

Such an anisotropic effect may be achieved in a number of ways. It may be accomplished by providing longitudinal reinforcement member(s) associated with the webbing. They may be incorporated through braiding techniques, by bonding/affixing stiffener(s) to the sleeve surface or by other means as would be apparent to one with skill in the art.

Regardless of the particulars of seal construction and whether it is utilized to provide a "hard" or "soft" user interface, the dual-sided seal disclosed provides a superior manner of carrying out the methodology noted above. Though a "soft" two-sided seal as shown in the figures is preferred for its elegance in approach and proven effectiveness, a "hard" or more complex "soft" seal approach might sometimes be desired.

In order to utilize the dual-sided seal in a "hard" approach, supplemental forcing means may be provided to apply pressure around seal waist (134). Mechanical means such as at least one of a strap, belt or cinch may be used. Alternately an inflatable cuff or bladder portions around the periphery of the seal may be employed. While the system complexity will increase due to provision for providing the supplemental pressure and controlling it by either automated or manual means, certain potential advantages arise. It may enable a single-evacuation procedure for chamber (104) rather than relying on constant or periodic vacuum replenishment. It may also provide greater design flexibility for seal (108). Particularly, by providing another variable to utilize in design decisions, a lesser emphasis may be placed on webbing material choice or opening sizing since the supplemental forcing capacity may be used to shape the seal as desired in use. Further, it may enable fitting seal (108) to a wider range of a populous for a given configuration of hard elements, such as those that make-up seal frame (110).

Supplemental forcing or seal shaping may also be used to produce a more complex "soft" seal than that described above. As with a "hard" seal approach, this would open design and fit possibilities. Forcing or seal shaping parameters may, again, be controlled manually or automatically. Except, in a complex "soft" seal, the control of pressure applied to waist (134) is gauged to provide a compliant feel or fit. Since the application of pressure on the seal interface with the user may be the only difference between a complex "soft" seal approach and a "hard" seal approach utilizing the dual-sided configuration, the same apparatus may be configured to function in either manner, for instance, by providing variable pressure control.

The negative pressure means and the warm medium contact means, described above, are typically actuatable, i.e., turned on and off, by a control means which controls actuation of the negative pressure means and the warming medium in response to whether thermal energy input is required to maintain the core body temperature of the mammal. The control means is generally a processing means that is capable of taking output data from the detecting means, i.e., data with respect to whether or not thermal energy input is required or not to maintain the core body temperature of the mammal, processing the data to determine whether or not the negative pressure means/warming means should be actuated or not and then actuating these components of the device accordingly

UTILITY

As demonstrated above, the subject methods provide a means for maintaining the core body temperature of a mammal at a substantially constant value under cold conditions. The subject methods are able to maintain the core body temperature of a mammal under cold conditions by introducing thermal energy or heat into the core body of a mammal in response to a detection of a requirement to do so in order to avoid a temperature drop in the core body temperature of a mammal. As such, the subject methods are suitable for use in a variety of different applications, where representative applications include maintaining the core body temperature of mammal at a substantially constant value under cold conditions for extended periods of time. As such, the subject methods and devices allow a mammal to remain in a cold environment for an enhanced period of time as compared to a control, e.g., an equally equipped individual without the subject methods and devices, without adverse effects on the individual. By enhanced period of time is meant an increase of at least about 1.2 fold, usually at least about 1.5 fold and more usually at least about 2.0 fold. Adverse effects that can be avoided using the subject methods include: impairment of physical ability, impairment of mental ability, etc. Accordingly, the subject methods and devices find use in applications where it is desirable for the individual to remain under cold conditions for extended periods of time, e.g., where individuals are working under cold conditions, e.g., in cold ocean water, in cold climates, etc.

It is evident from the above results and discussion that the subject invention provides a convenient means for maintaining the core body temperature of a mammal under cold conditions. Specifically, the subject invention is a non-invasive, simple to perform method and easy to use device which conveniently maintains the core body temperature of the mammal in a manner that is substantially non-interfering to the mammal, i.e., in a manner that is well tolerated and substantially not noticed by the mammal. Benefits of the subject methods and devices include the ability to dramatically extend the period of time that the mammal can be exposed to cold conditions without experiencing adverse effects, including physical and/or mental impairment. As such, the subject methods and devices find use in a variety of diverse applications, including applications in which they are employed to improve worker health and product under cold conditions, e.g., underwater and cold climate work environments. In view of the above discussion and results, it is readily apparent that the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method comprising:
   (a) detecting a requirement for thermal energy input in a mammal by detecting the presence of vasoconstriction in said mammal;
   (b) contacting a surface of a portion of said mammal in response to the presence of said requirement with a warm temperature medium under negative pressure conditions for a period of time sufficient to introduce thermal energy into the core body of said mammal; and
   (c) maintaining a substantially constant core body temperature of said mammal by maintaining the contact with said warm temperature medium.

2. The method according to claim 1, wherein said requirement is detected by detecting the presence of a thermoregulatory error in said mammal.

3. The method according to claim 1, wherein said method further comprises at least partially enclosing said portion of said mammal in a sealed enclosure to produce an enclosed portion of said mammal.

4. The method according to claim 1, wherein said method is a method of maintaining said core body temperature of said mammal substantially constant for a temporal duration of at least about 60 min and said method comprises performing steps (a), (b) and (c) at least twice during said temporal duration.

5. The method according to claim 1, wherein said portion of said mammal is a limb or a portion thereof.

6. The method according to claim 5, wherein said limb is selected from the group consisting of an arm and a leg.

7. The method according to claim 3, wherein said enclosure has a pressure ranging from about −20 to −80 mm Hg.

8. The method according to claim 1, wherein said warm temperature medium has a temperature ranging from about 44 to 48° C.

9. The method according to claim 1, wherein said period of time ranges from about 1 to 600 min.

10. The method according to claim 1, wherein said mammal is a human.

11. A method comprising:
    (a) monitoring a mammal during a temporal duration of at least about 60 minutes under cold conditions for the presence of a thermoregulatory error by detecting the presence of vasoconstriction in said mammal;
    (b) contacting a surface of an enclosed portion of said mammal in response to the presence of said thermoregulatory error with a warm temperature medium under negative pressure conditions for a period of time sufficient to introduce thermal energy into the core body of said mammal; and
    (c) maintaining a substantially constant core body temperature of said mammal under said cold conditions by maintaining the contact with said warm temperature medium.

12. The method according to claim 11, wherein said method further comprises at least partially enclosing said portion of said mammal in a sealed enclosure to produce an enclosed portion of said mammal.

13. The method according to claim 11, wherein said portion of said mammal is a limb or a portion thereof.

14. The method according to claim 13, wherein said limb is selected from the group consisting of an arm and a leg.

15. The method according to claim 12, wherein said enclosure has a pressure ranging from about −20 to −80 mm Hg.

16. The method according to claim 11, wherein said warm temperature medium has a temperature ranging from about 44 to 48° C.

17. The method according to claim 11, wherein said period of time ranges from about 60 to 600 min.

18. The method according to claim 11, wherein said mammal is a human.

19. A method comprising:
    (a) monitoring a mammal during a temporal duration of at least about 60 minutes under cold conditions for the presence of a vasoconstriction to detect a requirement for thermal energy input; and
    (b) contacting a surface of an enclosed portion of said mammal in response to the presence of said vasoconstriction with a warm temperature medium under negative pressure conditions ranging from about −20 to −80 mm Hg for a period of time ranging from about 1 to 600 min;
    (c) maintaining a substantially constant core body temperature of said mammal under said cold conditions by maintaining the contact with said warm temperature medium.

20. A device for introducing thermal energy into the core body of a mammal under cold conditions, said device comprising:
    (a) a means for detecting a requirement for thermal energy input in said mammal by detecting the presence of vasoconstriction in said mammal;
    (b) an enclosure for at least partially enclosing a portion of said mammal;
    (c) a negative pressure generator; and
    (d) a warmer.

21. The device according to claim 20, wherein said portion of said mammal is a limb or portion thereof.

22. The device according to claim 21, wherein said limb is selected from the group consisting of an arm and a leg.

23. The device according to claim 20, wherein said means for detecting a requirement for thermal energy input in said mammal is a means for detecting a thermoregulatory error in said mammal.

24. The device according to claim 23, wherein said means for detecting a requirement for thermal energy input in said mammal is a vasoconstriction detecting means.

25. The device according to claim 20, wherein said negative pressure generator is capable of producing a negative pressure ranging from about −20 to −80 mm Hg.

26. The device according to claim 20, wherein said mammal is a human.

27. The device according to claim 20, wherein said enclosure has a configuration selected from the group consisting of a sleeve, a glove and a boot.

* * * * *

UNITED STATES PATENT AND TRADEMARK OFFICE
CERTIFICATE OF CORRECTION

PATENT NO. : 6,966,922 B2
APPLICATION NO. : 10/655557
DATED : November 22, 2005
INVENTOR(S) : Dennis A. Grahn Page 1 of 1

It is certified that error appears in the above-identified patent and that said Letters Patent is hereby corrected as shown below:

In the Specification:

- In Column 1, prior to "1. Field of the Invention" beginning on line 15, insert the following header and paragraph:

--FEDERALLY SPONSORED RESEARCH AND DEVELOPMENT

This invention was made with Government support under contract NBCH1030020 awarded by The Department of the Interior, contract M67854-00-C-2144a, awarded by the Marine Corps Systems Command, and contracts DAMD17-03-2-0029, W911NF-05-1-0548, W911NF-07-1-0098 awarded by The Department of the Army. The Government has certain rights in this invention.--

Signed and Sealed this
Eighteenth Day of October, 2011

David J. Kappos
*Director of the United States Patent and Trademark Office*